United States Patent [19]
Dyer et al.

[11] Patent Number: 6,136,874
[45] Date of Patent: Oct. 24, 2000

[54] MICROPOROUS POLYMERIC FOAMS MADE WITH SILICON OR GERMANIUM BASED MONOMERS

[75] Inventors: John Collins Dyer; Herbert Louis Retzsch, both of Cincinnati, Ohio

[73] Assignee: The Procter & Gamble Company, Cincinnati, Ohio

[21] Appl. No.: 09/331,990

[22] PCT Filed: Dec. 5, 1997

[86] PCT No.: PCT/US97/22939

§ 371 Date: Jun. 30, 1999

§ 102(e) Date: Jun. 30, 1999

[87] PCT Pub. No.: WO98/29486

PCT Pub. Date: Jul. 9, 1998

Related U.S. Application Data

[60] Provisional application No. 60/034,156, Dec. 30, 1996.

[51] Int. Cl.$^7$ ...................................................... C08J 9/28
[52] U.S. Cl. .............................. 521/64; 521/63; 521/153; 521/154
[58] Field of Search ................................. 521/64, 63, 153, 521/154

[56] References Cited

U.S. PATENT DOCUMENTS

| | | | |
|---|---|---|---|
| 5,306,733 | 4/1994 | Adamski et al. | 521/64 |
| 5,340,842 | 8/1994 | Adamski et al. | 521/64 |

*Primary Examiner*—Morton Foelak
*Attorney, Agent, or Firm*—Carl J. Roof; Mary Catherine Hentz; Edward J. Milbrada

[57] ABSTRACT

Disclosed are polymeric foam materials obtained using monomers based on silicon and/or germination. The copolymerization of silicon- or germanium-based monomers provide foams that have low glass transition temperatures and low densities. These foams also exhibit relatively high yield stress values, which make the foams suitable for absorption of fluids, particularly aqueous fluids such as urine and menses (when the foams are rendered hydrophilic). The foams have a variety of other uses, including insulation applications.

24 Claims, 1 Drawing Sheet

MICROPOROUS POLYMERIC FOAMS MADE WITH SILICON OR GERMANIUM BASED MONOMERS

This is a 371 of PCT/US97/22939, filed on Dec. 5, 1997, which is a continuation-in-part of provisional application Ser. No. 60/034,156, filed on Dec. 30, 1996.

FIELD OF THE INVENTION

This application relates to microporous, open-celled polymeric foams made using monomers based on silicon or germanium.

BACKGROUND OF THE INVENTION

The development of microporous foams has been the subject of substantial commercial interest. Such foams have found utility in various applications, such as thermal, acoustic, electrical, and mechanical (e.g., for cushioning) insulators, absorbent materials, filters, membranes, carriers for inks, dyes, lubricants, and lotions, making items buoyant, and the like. References describing such uses and properties of foams include Oertel, G. "Polyurethane Handbook" Hanser Publishers, Munich, 1985, and Gibson, L. J.; Ashby, M. F. "Cellular Solids Structure and Properties" Pergamon Press, Oxford, 1988. The term "insulator" refers to any material which reduces the transfer of energy from one location to another. The term "absorbent" refers to materials which imbide and hold or distribute fluids, usually liquids, an example being a sponge. The term "filter" refers to materials which pass a fluid, either gas or liquid, while retaining impurities within the material by size exclusion. Other uses for foams are generally obvious to one skilled in the art.

For many uses, composite and generally conflicting requirements are placed on the foam itself. These may include (1) low density, (2) flexibility, (3) strength (compressive and tensile), (4) openness, and (5) control of morphology. Low density foams are more efficient since most uses require a certain volume and a low density foam will impose less mass to meet this objective. Flexible foams are typically generated by maintaining a relatively low glass transition temperature ("Tg") of the foam. Strength is a parameter which is inevitably sacrificed to achieve either lower Tg or lower density. Strength can be generated effectively by including crosslinking agents which link the polymeric chains of the foam together in a fashion which confers a degree of resistance to deformation and the ability to recover from deformation, e.g., elasticity. Openness and morphology are controlled principally by the method of foam formation and curing.

Accordingly, it would be desirable to be able to make an open-celled, high surface area polymeric foam material that: (1) has the lowest density consistent with the other requirements imposed on the foam; (2) is flexible; (3) is strong; (4) has a generally open-celled structure; and (5) can be manufactured so as to control the size of cells produced within the foam.

SUMMARY OF THE INVENTION

The present invention relates to polymeric foams comprising comonomers based on silicon and/or germanium. The term "comonomer" is used herein to denote that these required comonomers are generally to be used with other comonomers which may or may not contain silicon and/or germanium. These polymeric foams are preferably prepared by polymerization of certain water-in-oil emulsions having a relatively high ratio of water phase to oil phase, commonly known in the art as high internal phase emulsions, or "HIPEs". As used herein, polymeric foam materials which result from the polymerization of such emulsions are referred to hereafter as "HIPE foams." The HIPE foam materials of the present invention comprise a generally flexible, semi-flexible, or rigid nonionic polymeric foam structure of interconnected open-cells. Comonomers used to form HIPEs generally must be relatively insoluble in the aqueous phase of the emulsion.

The polymeric foam structures that are derived from HIPEs comprise at least about 5%, based on the weight of the foam, of one or more comonomer(s) selected from the group consisting of silicon-containing comonomers, germanium-containing comonomers, and mixtures thereof.

Preferably, the foams of the present invention will have:

A) a density of less than about 0.10 g/cc;

B) a glass transition temperature (Tg) of between about −40° and 90° C.; and

C) a yield stress value of at least about 0.25 psi.

The present invention relates to foams prepared via polymerization of a HIPE comprising a discontinuous water phase and a continuous oil phase wherein the ratio of water to oil is at least about 10:1. The water phase generally contains an electrolyte and a water soluble initiator. The oil phase generally consists of substantially water-insoluble monomers polymerizeable by free radicals, including at least one comonomer which contains silicon and/or germanium, an emulsifier, and other optional ingredients defined below. The monomers which contain silicon and/or germanium are selected so as to confer the properties desired in the resulting polymeric foam, e.g. low density, a glass transition (Tg) between about −40° and 90° C., mechanical integrity sufficient for the intended end use, and an open-celled, microporous morphology.

DETAILED DESCRIPTION OF THE INVENTION

I. Polymeric Foams Containing Silicon and/or Germanium

Polymeric foams of the present invention are comprised of specific combinations of monomers which to a large extent control the ultimate properties of the foam. The types of monomers used fall into the following three general categories: (1) monomers which help maintain a desirable Tg in the resulting polymer, (2) monomers which help confer "toughness" to the resulting polymer, herein referred to as "toughening monomers", and (3) monomers which have di-, tri-, tetra-, and higher functionality useful in conferring crosslinks within the resulting polymer, herein referred to as crosslinkers. These crosslinks are particularly critical in achieving the desired comprehensive strength or modulus and/or elasticity which is required for many foam applications. Applicants have discovered that, surprisingly, monomers which contain silicon and/or germanium are particularly useful in areas (1) and (3) above. For example, a comonomer such as (3-acryloxypropyl)methylbis (trimethylsiloxy)silane (referred to hereinafter as APMTS) forms polymers which have desirably low Tgs. As another example, a crosslinker such as tetrakis(2-methacryloxyethoxy)silane (referred to hereinafter as TKMES) forms polymers which are effectively crosslinked so as to have desirable compressive strength and elasticity without increasing the Tg of the resulting polymeric foam to an undesirable degree. The general class of such compounds is described more completely hereinafter, though these two are presented as being generally illustrative, nonrestrictive examples of the invention. It is understood that both of these representative examples are used as comonomers with other comonomers to confer the properties desired in the ultimate foam.

The ability of these silicon and/or germanium based comonomers to confer the desired strength without increasing the Tg undesirably is thought to relate to the molecular flexibility associated with bonds attached to the Si and/or Ge atom. This flexibility is seen in polysiloxanes which have very low Tgs. In contrast, comonomers which confer strength while lacking sufficient molecular flexibility tend to increase Tg. Examples include divinyl benzene, a crosslinker wherein higher levels may increase the strength of the polymer while also increasing the Tg. Tg is an important criterion in the use of any polymer. While in some uses a relatively high Tg may be desired, in general this is more easily accomplished than achieving a corresponding low Tg in a polymer without sacrificing other properties such as strength to an undesirable degree. Applicants have found that the comonomers used in the present invention are particularly useful in maintaining a comparatively low Tg while also conferring sufficient strength for many uses in the final product.

The polymers that constitute the present foams comprise from about 0.5% to about 30% elemental silicon or germanium, or a combination of the two. Preferably, the polymer will comprise from about 1% to about 15%, more preferably from about 2% to about 10%, of these elements. While the foams may be described in terms of their elemental silicon/germanium content, it is understood that these elements are covalently bound to other polymerizeable groups and are introduced into the foam's polymer in the form of silicon/germanium-containing comonomers.

II. General Foam Characteristics

The polymeric foams of the present invention are relatively open-celled. This means the individual cells of the foam are in complete, unobstructed communication with adjoining cells. The cells in such substantially open-celled foam structures have intercellular openings or "windows" connecting one cell to another within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2. As used herein, a foam material is "open-celled" if at least 80% of the cells in the foam structure that are at least 1 $\mu$m in size are in open communication with at lest one adjacent cell.

These polymeric foams may generally be hydrophobic to inhibit the passage of aqueous fluids through the foam, or hydrophilic to encourage imbibition of aqueous fluids into the foam. The hydrophobic/hydrophilic properties of the internal surfaces of the foam structures are controlled by post-polymerization foam treatment procedures. As used herein, the term "hydrophilic" is used to refer to surfaces that are wettable by aqueous fluids deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion,* edited by Robert F. Gould (Copyright 1964), which is hereby incorporated herein by reference. A surface is said to be wetted by a fluid (i.e., hydrophilic) when either the contact angle between the fluid and the surface is less than 90°, or when the fluid tends to spread spontaneously across the surface, both conditions normally co-existing. Conversely, a surface is considered to be "hydrophobic" if the contact angle is greater than 90° and the fluid does not spread spontaneously across the surface.

The foams used according to the present invention are readily optimized so as to confer the properties desired in each specific application. As examples, these foams may be microcellular (<10 $\mu$m) up through moderate cell diameters (ca. 150 $\mu$m); low density (0.10 g/cc) to very low density (0.004 g/cc); rigid to flexible (corresponding, high Tg to low (subambient) Tg); and strong to weak. The foams may be provided as continuous sheets, rigid thick boards, particulates of various sizes, specific shapes, etc., as required by their end use. However optimized, these foams avoid some of the deficiencies associated with the foam methods described hereinabove. That is, they generally contain little or no nitrogen or sulfur so that burning produces no unusually noxious gases, require no CFC or volatile organic compound ("VOC") materials during manufacture, are generally photostable, are producible readily in large quantities with reasonable economics as either slabstock, roll stock, particulate foam, and the like.

A. Glass Transition Temperature

A key parameter of the foams of the present invention is their glass transition temperature (Tg). The Tg represents the midpoint of the transition between the glassy and rubbery states of the polymer. Foams that have a Tg higher than the temperature of use can be very strong but can also be very rigid and potentially prone to fracture. Such foams also typically take a long time to recover to the expanded state after having been stored in the compressed state for prolonged periods. Though the end use of a particular foam is an important factor when determining the desired Tg of the foam, preferred are foams having a Tg of from about 15° to about 50° C. More preferred are foams having a Tg of from about 20° to about 40° C. The silicon and/or germanium containing comonomers described hereinafter are particularly useful in developing low Tg polymers. The method for determining Tg by Dynamic Mechanical Analysis (DMA) is described in the TEST METHODS section infra.

B. Foam Density

Another important property of the foams of the present invention is their density. "Foam density" (i.e., in grams of foam per cubic centimeter of foam volume in air) is specified herein on a dry basis, unless otherwise indicated. Any suitable gravimetric procedure that will provide a determination of mass of solid foam material per unit volume of foam structure can be used to measure foam density. For example, an ASTM gravimetric procedure described more fully in the TEST METHODS section of U.S. Pat. No. 5,387,207 (Dyer et al.), issued Feb. 7, 1995 (incorporated by reference herein) is one method that can be employed for density determination. While foams can be made with virtually any density ranging from below that of air to just less than the bulk density of the polymer from which it is made, the foams of the present invention are most useful when they have a dry density in the expanded state of less than about 0.10 g/cc, preferably between about 0.08 and about 0.004 g/cc, more preferably between about 0.04 and 0.01 g/cc, and most preferably about 0.02 g/cc.

C. Cell Size

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

Figure 1:
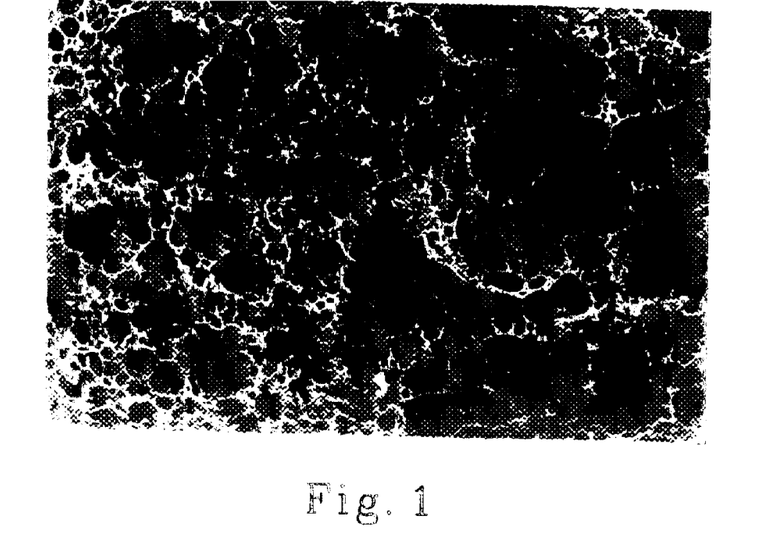
FIG. 1 of the drawings is a photomicrograph (250× magnification) of a cut section of a representative polymeric foam of the present invention made from a HIPE having a 60:1 water-to-oil weight ratio and formed at 55° C., where the monomer component consisted of a 55:33:12 weight ratio of 2-ethylhexyl acrylate (EHA):divinyl benzene (about 40% DVB and about 60% ethyl styrene):tetrakis(3-methacryloxyethoxy)silane, and where 10% (by weight of the oil phase) of diglycerol monooleate (DGMO) emulsifier was used.
Figure 2:
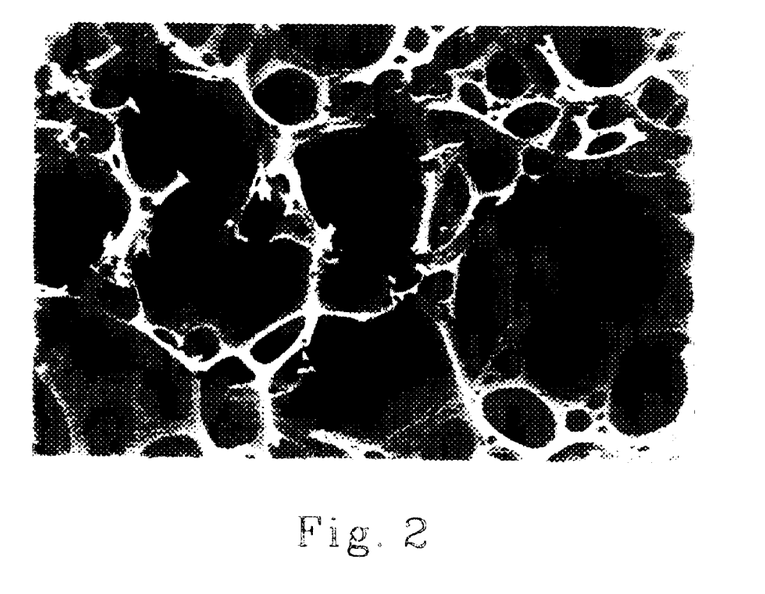
FIG. 2 of the drawings is a photomicrograph (1000× magnification) of the foam of FIG. 1.

A number of techniques are available for determining the average cell size of foams. The most useful technique, however, for determining cell size in foams involves a simple measurement based on the scanning electron photomicrograph of a foam sample. FIG. 1, for example, shows a typical HIPE foam structure according to the present invention. Superimposed on the photomicrograph is a scale representing a dimension of 100 μm. Such a scale can be used to determine average cell size via an image analysis procedure.

The cell size measurements given herein are based on the number average cell size of the foam, e.g., as shown in FIG. 1. The foams of the present invention will preferably have a number average cell size of not more than about 150 μm, more preferably from about 10 to 100 μm, and most preferably from about 15 μm to 35 μm. As with other foam characteristics, the preferred average cell size for a given foam will be dictated in-part by its anticipated end use.

D. Specific Surface Area

Another important parameter of the foams is their specific surface area, which is determined by both the dimensions of the cellular units in the foam and by the density of the polymer, and is thus a way of quantifying the total amount of solid surface provided by the foam. Specific surface area is determined by measuring the amount of capillary uptake of a low surface tension liquid (e.g., ethanol) which occurs within a foam sample of known mass and dimensions. A detailed description of such a procedure for determining foam specific surface area via the capillary suction method is set forth in the TEST METHODS section of U.S. Pat. No. 5,387,207 (Dyer et al.), issued Feb. 7, 1995, which is incorporated herein by reference. Other similar tests for determining specific surface area can be used with the present foams.

The foams of the present invention have a specific surface area of at least about 0.01 m$^2$/cc, preferably at least about 0.025 m$^2$/cc.

E. Yield Stress

Yield stress is determined in a stress-strain experiment conducted on the foam at a specified temperature and rate of strain (in compression mode). The yield stress is the stress at the transition from the linear elastic region to the plateau region of the stress-strain curve. Yield stress is indicative of the general strength properties of the polymeric foam at the temperature of interest. For many applications, higher yield stress values are desirable at a given foam density and Tg. The foams of the present invention will preferably have a yield stress value of at least about 0.25 psi, preferably at least about 0.5 psi.

III. Foam Uses

The polymeric foams of the present invention will have numerous end uses. For example, the foams may be prepared to be absorbent materials, particularly for aqueous based fluids such as urine and menses. Such foams will be prepared to have the structural characteristics similar to the HIPE-derived foams described in, e.g., copending U.S. patent application Ser. No. 08/563,866 (DesMarais et al., filed Nov. 29, 1995); copending U.S. patent application Ser. No. 08/542,497 (Dyer et al., filed Oct. 13, 1995); U.S. Pat. No. 5,387,207 (Dyer et al., issued Feb. 7, 1995); U.S. Pat. No. 5,550,167 (DesMarais, issued Aug. 27, 1996); and U.S. Pat. No. 5,563,179 (DesMarais et al., issued Oct. 8, 1996); each of which is incorporated by reference herein. Such absorbent foams may be included in absorbent articles such as infant diapers, femanine hygiene articles (e.g., tampons, catamenial pads), adult incontinence articles, and the like, such as those described in the aforementioned copending patent applications and issued patents. The foams may also be prepared so as to be useful as insulators. Such foams will have structural characteristics (e.g., cell size, density, Tg) similar to the foams described in copending U.S. patent application Ser. No. 08/472,447 (Dyer et al., filed Jun. 7, 1995) and copending U.S. patent application Ser. No. 08/484,727 (DesMarais et al., filed Jun. 7, 1995, both of which are incorporated by reference herein. The polymeric foams may also be used for filters of fluids (liquid or gas), to remove impurities. Other uses for foams include membranes, carriers for inks, dyes, lubricants, lotions, making items buoyant, and other uses generally obvious to one skilled in the art.

III. Preparation of Polymeric Foams From HIPEs Using Monomers Containing Silicon and/or Germanium A. In General Polymeric foams of the present invention are preferably prepared by polymerization of HIPEs. The relative amounts of the water and oil phases used to form the HIPEs are, among many other parameters, important in determining the structural, mechanical and performance properties of the resulting polymeric foams. In particular, the ratio of water to oil in the emulsion can influence the density, cell size, and specific surface area of the foam and dimensions of the struts that form the foam. The emulsions used to prepare the HIPE foams will generally have a volume to weight ratio of water phase to oil phase of at least about 10:1, preferably from about 12.5:1 to about 250:1, more preferably from about 25:1 to about 75:1, and most preferably about 50:1.

The process for obtaining these foams comprises the steps of:

(A) forming a water-in-oil emulsion under low shear mixing from:
  (1) an oil phase comprising:
    (a) from about 80% to about 98% by weight of a monomer component capable of forming a copolymer having a Tg value of from about 40° C. to about 90° C., said monomer component comprising:
      (i) at least about 5% by weight of a material selected from the group consisting of one or more comonomers containing silicon, one or more comonomers containing germanium, and mixtures thereof;
      (ii) from about 0% to about 70% by weight of a substantially water-insoluble, monofunctional monomer capable of forming a homopolymer having a Tg of about 40° C. or less;
      (iii) from about 0% to about 70% by weight of a substantially water-insoluble, monofunctional comonomer capable of imparting toughness about equivalent to that provided by styrene;

(iv) from about 0% to about 50% of a first substantially water-insoluble, polyfunctional crosslinking agent selected from the group consisting of divinyl benzene and analogs thereof; and (v) from about 0% to about 15% of a second substantially water-insoluble, polyfunctional crosslinking agent selected from the group consisting of diacrylates and dimethacrylates of diols and analogs thereof; and (b) from about 2% to about 20% by weight of an emulsifier component which is soluble in the oil phase and which is suitable for forming a stable water-in-oil emulsion;

(2) a water phase comprising from about 0.1% to about 20% by weight of a water-soluble electrolyte; and (3) a volume to weight ratio of water phase to oil phase of at least about 10:1; and (B) polymerizing the monomer component in the oil phase of the water-in-oil emulsion to form the polymeric foam material.

The polymeric foam material can be subsequently iteratively washed and dewatered to provide a dry, hydrophobic foam. Alternatively, the foam may be rendered hydrophilic by appropriate surface treatment with any of a number of hydrophilizing agents, including calcium chloride and similar salts, residual emulsifiers used for stabilizing the HIPE, and other wetting agents well known to those skilled in the art. Hydrophilizing treatments are described in, e.g., U.S. Pat. No. 5,387,207 (Dyer et al., issued Feb. 7, 1995) (see especially column 22 to column 24), which is incorporated herein by reference.

These foams may be shaped as desired. Typically, this shaping will comprise slicing into relatively thin sheets. These sheets may optionally be compressed, e.g. continuously through pressure nips, into a thin state and wound into rolls. Compressible sheets will retain their relatively thin compressed state until unwound, applied as desired, and either heated above their activation temperature (usually about the Tg of the polymer) or allowed to stand for a relatively long period of time, e.g. several weeks or months, depending on the ambient temperature, as described in copending U.S. patent application Ser. No. 08/484,727 (DesMarais et al., filed Jun. 7, 1995). Alteratively, the shapes may be conferred by the shape of the vessel in which the HIPE is cured so as to form the polymeric foam material. Alternatively, the cured foam may be diced, shredded, ground, or otherwise comminuted into small particulate pieces for further use.

1. Oil Phase Components

The continuous oil phase of the HIPE comprises comonomers that are polymerized to form the solid foam structure. This monomer component is formulated to be capable of forming a copolymer having a Tg of from about −40° to about 90° C., and preferably from about 15° to about 50° C., more preferably from about 20° to about 40° C. (The method for determining Tg by Dynamic Mechanical Analysis (DMA) is described in the TEST METHODS section infra.) This monomer component includes at least one of a comonomer, at a level of at least about 5%, that contains silicon and/or germanium. Preferably, the monomer component will include from about 8% to about 50%, more preferably from about 10% to about 30%, of a comonomer (s) containing silicon and/or germanium. Levels of such comonomers lower than about 5% are found to induce minimally measurable changes in the foam properties. This monomer component may further include: (a) at least one monofunctional comonomer whose atactic amorphous homopolymer has a Tg of about 40° C. or lower (see Brandup, J.; Immergut, E. H. "Polymer Handbook", 2nd Ed., Wiley-Interscience, New York, N.Y., 1975, III-139.), described hereinafter as a "Tg lowering monomer"; (b) at least one monofunctional comonomer to improve the toughness or tear resistance of the foam, described hereinafter as a "toughening monomer"; (c) a first polyfunctional crosslinking agent; and/or (d) optionally a second polyfunctional crosslinking agent. The comonomers described above in section (a), (b), and (c) may also contain silicon and/or germanium to satisfy the level requirements for these elements in the formulation. The selection of particular types and amounts of monofunctional monomer(s) and comonomer(s) and polyfunctional cross-linking agent(s) can be important to the realization of absorbent HIPE foams having the desired combination of structure, and mechanical properties which render such materials suitable for use in the invention herein.

The monofunctional comonomer components which contain silicon and/or germanium include myriad types. These can include comonomers designed to serve as Tg lowering monomers, as defined above. Examples generally include monomers having at least one pendant group which is reactive in free radical polymerizations. Nonlimiting examples of such pendant groups include acrylates, methacrylates, acrylamides, methacrylamides, styryls, dienes, vinyl sulfones, and the like. Such pendant groups are well known to those skilled in the art. Attached to these pendant groups will be a moiety containing at least one silicon and/or germanium atom appropriately functionalized. Nonlimiting examples of these moieties include dimethylsiloxanes, germanoxanes, silanes, and germanes. Preferred examples are silicon-containing Tg lowering monomers which contain di- and trisiloxane moieties, for example, the groups —Si(CH$_3$)$_2$—)—O—Si(CH$_3$)$_2$— and —Si(CH$_3$)$_2$—)—O—Si(CH$_3$)$_2$—O—Si(CH$_3$)$_2$—. These moieties provide an exceptionally flexible side chain on the pendant reactive group which, after polymerization, induces a strong Tg lowering effect on a weight basis. It has been found by experiment that at least about 5% of these monomers must be used to exert the desired influence. Since these monomers typically contain between about 10% and about 40% elemental silicon and/or germanium, the amount of elemental silicon and/or germanium in the formulation typically will be at least about 0.5%. The upper range in the amount of silicon and/or germanium used in the formulation is governed by the maximum amount of such comonomers that can be used, which is 100% times the maximum level of silicon and/or germanium possible in the comonomer while retaining the reactive pendant group, which is about 50% in the case of trimethylvinyl germane. Specific nonlimiting examples of monomers include (3-acryloxypropyl)-methylbis-(trimethylsiloxy)silane, allyltriisopropyl silane, allyltriphenyl silane, bis(trimethylsilyl)itaconate, p-(t-butyldimethylsiloxy)styrene, methacrylamidopropyltriethoxysilane, methacryloxyethoxytrimethylsilane, (methacryloxymethyl)-dimethylethoxysilane, methacryloxytrimethyl silane, (2,4-pentadienyl)trimethylsilane, styrylethyltrimethoxysilane, 3-(N-styrylmethyl-2-aminoethylamino)propyltrimethoxy-silane hydrochloride, (m,p-vinylbenzyloxy)trimethylsilane, vinyltrimethyl silane, vinyldimethylethyl silane, vinylpentamethyldisiloxane, vinyl trifluoromethyldimethyl silane, vinyltris(trimethylsiloxy)silane, and vinyltriethyl germane. While each of these examples will vary in their propensity to serve as a Tg lowering monomer, each may find specific advantage in achieving a specific Tg for a polymeric foam needed for a particular end use.

The monomer component may include one or more other Tg lowering monofunctional monomers that do not contain silicon and/or germanium that tend to impart rubber-like properties to the resulting polymeric foam structure. Such monomers can produce high molecular weight (greater than 10,000) atactic amorphous homopolymers having Tgs of about 40° C. or lower. Monomers of this type include, for example, the $C_4$–$C_{14}$ alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate, tetradecyl acrylate; aryl and alkaryl acrylates such as benzyl acrylate and nonylphenyl acrylate; the $C_6$–$C_{16}$ alkyl methacrylates such as hexyl methacrylate, octyl methacrylate, nonyl methacrylate decyl methacrylate, isodecyl methacrylate, dodecyl (lauryl) methacrylate, and tetradecyl methacrylate; acrylamides such as N-octadecyl acrylamide; $C_4$–$C_{12}$ alkyl styrenes such as p-n-octylstyrene; and combinations of such monomers. Of these monomers, isodecyl acrylate, dodecyl acrylate and 2-ethylhexyl acrylate are the most preferred. These monofunctional monomer(s) will generally comprise 0 to about 70%, more preferably from about 20 to about 60%, by weight of the monomer component.

The monomer component utilized in the oil phase of the HIPEs may also comprise one or more monofunctional comonomers capable of imparting toughness about equivalent to that provided by styrene to the resulting polymeric foam structure. Tougher foams exhibit the ability to deform substantially without failure. These monofunctional comonomer types can include styrene-based comonomers (e.g., styrene and ethyl styrene) or other monomer types such as methyl methacrylate where the related homopolymer is well known as exemplifying toughness. The preferred monofunctional comonomer of this type is a styrene-based monomer with styrene and ethyl styrene being the most preferred. The monofunctional "toughening" comonomer will normally comprise from about 0 to about 70%, preferably from about 20% to about 50%, most preferably from about 30% to about 50%, by weight of the monomer component.

In certain cases, the "toughening" comonomer can also impart the desired rubber-like properties to the resultant polymer. For such comonomers, the amount that can be included in the monomer component will be that of the typical monomer and comonomer combined.

The monomer component contains a first (and optionally a second) polyfunctional crosslinking agent. As with the monofunctional monomers and comonomers, selection of the particular type and amount of crosslinking agent(s) is important to the realization of polymeric foams having the desired combination of structural and mechanical properties. It has also been found that such crosslinkers can advantageously contain silicon and/or germanium.

The first polyfunctional crosslinking agent can be selected from monomers containing silicon and/or germanium. Generally, these comprise a relatively central silicon and/or germanium atom functionalized with at least two of the pendant reactive groups described hereinabove. Preferred examples have 3 or 4 pendant reactive groups are based on silicon, though germanium can generally be substituted as well. Nonlimiting examples include tetraallyl silane (abbreviated "TAS"), tetrakis(2-methacryloxyethoxy)silane ("TKMES"), 1,3-bis(3-methacryloxypropyl)tetramethyldisiloxane ("BMPTDS"), and 1,3,5-trivinyl-1,1,3,5,5-pentamethyltrisiloxane ("TVPTS"). Other nonlimiting examples include dimethoxydiallyl silane, bis(2-allyloxymethyl)-1-trimethylsiloxybutane, bis(methacryloxy)diphenylsilane, bis(methacryloxy)dimethyl silane, bis(4-styryl)dimethylsilane, diallyldiphenylsilane, diallyldimethylsilane, 1,3-diallyltetramethyldisiloxane, divinyltetramethyldisiloxane, hexavinyldisiloxane, bis(2-allyloxymethyl)phenethyl)-tetramethyldisiloxane, 1,5-divinylhexamethyltrisiloxane, and tetraallyl germane. It has been found by experimentation that these crosslinkers can be used to strengthen the polymer efficiently without unduly increasing the Tg of the polymer, which may not be disired in all cases. The polyfunctional silicon- or germanium-containing "crosslinking" comonomer will normally comprise from about 5 to about 80%, preferably from about 10% to about 60%, most preferably from about 25% to about 40%, by weight of the monomer component.

The first polyfunctional crosslinking agent can also be selected from a wide variety of monomers containing two or more activated vinyl groups, such as divinylbenzenes and analogs thereof. Analogs of divinylbenzenes useful herein include, but are not limited to, trivinyl benzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof. Divinylbenzene is typically available as a mixture with ethyl styrene in proportions of about 55:45. These proportions can be modified so as to enrich the oil phase with one or the other component. Generally, it is advantageous to enrich the mixture with the ethyl styrene component while simultaneously reducing the amount of styrene in the monomer blend. The preferred ratio of divinylbenzene to ethyl styrene is from about 30:70 to 55:45, most preferably from about 35:65 to about 45:55. The inclusion of higher levels of ethyl styrene imparts the required toughness without increasing the Tg of the resulting copolymer to the degree that styrene does. This first cross-linking agent can generally be included in the oil phase of the HIPE in an amount of from about 2 to about 50%, more preferably from about 10 to about 35%, most preferably from about 15% to about 25%, by weight of the monomer component (on a 100% basis).

The optional second crosslinking agent can be selected from polyfunctional acrylates or methacrylates selected from the group consisting of diacrylates or dimethacrylates of diols and analogs thereof. Such crosslinking agents include methacrylates, acrylamides, methacrylamides, and mixtures thereof. These include di-, tri-, and tetra-acrylates, as well as di-, tri-, and tetra-methacrylates, di-, tri-, and tetra-acrylamides, as well as di-, tri-, and tetra-methacrylamides; and mixtures of these crosslinking agents. Suitable acrylate and methacrylate crosslinking agents can be derived from diols, triols and tetraols that include 1,10-decanediol, 1,8-octanediol, 1,6-hexanediol, 1,4-butanediol, 1,3-butanediol, 1,4-but-2-enediol, ethylene glycol, diethylene glycol, trimethylolpropane, pentaerythritol, hydroquinone, catechol, resorcinol, trimethyl glycol, polyethylene glycol, sorbitol and the like. (The acrylamide and methacrylamide crosslinking agents can be derived from the equivalent diamines, triamines and tetramines). The preferred diols have at least 2, more preferably at least 4, most preferably 6, carbon atoms. This second cross-linking agent can generally be included in the oil phase of the HIPE in an amount of from 0 to about 15% by weight of the monomer component.

The major portion of the oil phase of the HIPEs will comprise the aforementioned monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase of the HIPE is an emulsifier component that comprises at least a primary emulsifier. Suitable primary emulsifiers are well known to those skilled in the art. Particularly preferred emulsifiers include Span 20™, Span 40™, Span 60™, and Span 80™. These are nominally esters of sorbitan derived from lauric, myristic, stearic, and oleic acids, respectively. Other preferred emulsifiers include the diglycerol esters derived from monooleate, monomyristate, monopalmitate, and monoisostearate acids. A preferred coemulsifier is ditallowdimethyl ammonium methyl sulfate. Mixtures of these emulsifiers are also particularly useful, as are purified versions of each, specifically sorbitan esters containing minimal levels of isosorbide and polyol impurities.

When an optional secondary emulsifier(s) is included in the emulsifier component, it is typically at a weight ratio of primary to secondary emulsifier of from about 50:1 to about 1:4, preferably from about 30:1 to about 2:1.

As is indicated, those skilled in the art will recognize that any suitable emulsifier(s) can be used in the processes for making the foams of the present invention. For examples, see U.S. Pat. No. 5,387,207 and U.S. Pat. No. 5,563,179.

The oil phase used to form the HIPEs comprises from about 80 to about 98% by weight monomer component and from about 2 to about 20% by weight emulsifier component. Preferably, the oil phase will comprise from about 90 to about 97% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference.

A preferred optional component is an antioxidant such as a Hindered Amine Light Stabilizer (HALS) such as bis-(1,2,2,5,5-pentamethylpiperidinyl) sebacate (Tinuvin-765®) or a Hindered Phenolic Stabilizer (HPS) such as Irganox-1076® and t-butylhydroxy-quinone. Another preferred optional component is a plasticizer such as dioctyl azelate, dioctyl sebacate or dioctyl adipate. Yet another optional ingredient is filler particles which may toughen the polymer and/or increase its thermal insulating properties. Example filler particules include aluminum, titanium dioxide, carbon black, graphite, calcium carbonate, talc, and the like. Generally, particles which help make the polymer opaque in the infrared region are preferred, such as carbon black and graphite. Other optional components include colorants (dyes or pigments), fluorescent agents, opacifying agents, chain transfer agents, and the like.

2. Water Phase Components

The discontinuous water internal phase of the HIPE is generally an aqueous solution containing one or more dissolved components. One essential dissolved component of the water phase is a water-soluble electrolyte. The dissolved electrolyte minimizes the tendency of monomers, comonomers, and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in preparing the HIPEs. Generally the electrolyte will be utilized in the water phase of the HIPEs in a concentration in the range of from about 0.2 to about 20% by weight of the water phase. More preferably, the electrolyte will comprise from about 1 to about 10% by weight of the water phase.

The HIPEs will also typically contain an effective amount of a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants and Hydratable Salts

The polymer forming the HIPE foam structure will preferably be substantially free of polar functional groups. This means the polymeric foam will be relatively hydrophobic in character. When these foams are to be used as insulating materials, resistance to water is generally a desired feature. Removal of the residual emulsifier and/or salt following polymerization is generally desired in a manner described more fully hereafter.

B. Processing Conditions for Obtaining HIPE Foams

Foam preparation typically involves the steps of: 1) forming a stable high internal phase emulsifier (HIPE); 2) polymerizing/curing this stable emulsion under conditions suitable for forming a solid polymeric foam structure; 3) optionally washing the solid polymeric foam structure to remove the original residual water phase, emulsifier, and salts from the polymeric foam structure; 4) thereafter dewatering this polymeric foam structure; and 5) optionally hydrophilizing the foam.

1. Formation of HIPE

The HIPE is formed by combining the oil and water phase components in the previously specified ratios. The oil phase will typically contain the requisite monomers, comonomers, crosslinkers, and emulsifiers, as well as optional components such as plasticizers, antioxidants, flame retardants, and chain transfer agents. The water phase will typically contain electrolytes and polymerization initiators.

The HIPE can be formed from the combined oil and water phases by subjecting these combined phases to shear agitation. Shear agitation is generally applied to the extent and for a time period necessary to form a stable emulsion. Such a process can be conducted in either batchwise or continuous fashion and is generally carried out under conditions suitable for forming an emulsion where the water phase droplets are dispersed to such an extent that the resulting polymeric foam will have the requisite structural characteristics. Emulsification of the oil and water phase combination will frequently involve the use of a mixing or agitation device such as a pin impeller.

One preferred method of forming HIPE involves a continuous process that combines and emulsifies the requisite oil and water phase. In such a process, a liquid stream comprising the oil phase is formed. Concurrently, a separate liquid stream comprising the water phase is also formed. The two separate streams are then combined in a suitable mixing chamber of zone such that the requisite water to oil phase weight ratios previously specified are achieved.

In the mixing chamber or zone, the combined streams are generally subjected to shear agitation provided, for example, by a pin impeller of suitable configuration and dimensions. Shear will typically be applied to the combined oil/water phase stream at an appropriate rate. Once formed, the stable liquid HIPE can then be withdrawn from the mixing chamber or zone. This preferred method for forming HIPEs via a continuous process is described in greater detail in U.S. Pat. No. 5,149,720 (DesMarais et al.), issued Sep. 22, 1992, which is incorporated by reference. See also copending U.S. application Ser. No. 08/370,694, filed Jan. 10, 1995 by T. DesMarais (incorporated herein by reference), which describes an improved continuous process having a recirculation loop for the HIPE.

2. Polymerization/Curing of the HIPE

The HIPE formed will generally be formed, collected, or poured in a suitable reaction vessel, container or region to be polymerized or cured. In one embodiment, the reaction vessel is constructed of polyethylene from which the eventually polymerized/cured solid foam material can be easily removed for further processing after polymerization/curing has been carried out to the extent desired. The temperature at which the HIPE is poured into the vessel is generally about the same as the polymerization/curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 30° C., more preferably above about 35° C., for a time period ranging from about 2 to about 64 hours, more preferably from about 4 to about 48 hours. The HIPE can also be cured in stages such as described in U.S. Pat. No. 5,189,070 (Brownscombe et al.) issued Feb. 23, 1993, which is herein incorporated by reference.

A porous water-filled open-celled HIPE foam is typically obtained after polymerization/curing in a reaction vessel, such as a cup or tub. This polymerized HIPE foam is typically cut or sliced into a sheet-like form. Sheets of polymerized HIPE foam are easier to process during subsequent treating/washing and dewatering steps, as well as to prepare the HIPE foam for use in insulation materials. The polymerized HIPE foam is typically cut/sliced to provide a cut thickness in the range of from about 0.08 in. to about 3.5 in.

3. Treating/Washing HIPE Foam

The polymerized HIPE foam formed will generally be filled with residual water phase material used to prepare the HIPE. This residual water phase material (generally an aqueous solution of electrolyte, residual emulsifier, and polymerization initiator) may be removed prior to further processing and use of the foam. Removal of this original water phase material will usually be carried out by compressing the foam structure to squeeze out residual liquid and/or by washing the foam structure with water or other aqueous washing solutions. Frequently, several compressing and washing steps, e.g., from 2 to 4 cycles, will be desirable. It is preferable that the water used in these washing be heated to at least about the Tg of the polymer so as to maintain its flexibility and compliance during compressive dewatering and to reduce and prevent damage to the foam structure.

4. Foam Dewatering

After the HIPE foam has been treated/washed, it will be dewatered. Dewatering can be achieved by compressing the foam to squeeze out residual water, by subjecting the foam or the water therein to temperatures of from about 60° to about 200° C. or to microwave treatment, by vacuum dewatering or by a combination of compression and thermal drying/microwave/vacuum dewatering techniques. These HIPE foams are typically compressively dewatered to a thickness of about ⅓ (33%) or less of their fully expanded thickness. The dewatering step will generally be carried out until the HIPE foam is ready for use and is as dry as practicable. Frequently such compression dewatered foams will have a water (moisture) content of from about 1% to about 15%, more preferably from about 5% to about 10% by weight on a dry weight basis.

5. Foam Hydrophilization

When hydrophilic foams are desired (e.g., for use in absorbent articles), it may be desirable to treat the washed, dewatered foam with a hydrophilizing agent. Suitable hydrophilizings agents and methods for hydrophilizing foams are disclosed fully at, e.g., column 22 to column 24 of U.S. Pat. No. 5,387,207.

IV. Test Methods

Samples are prepared for evaluation by slicing into 3 to 8 mm thick pieces and stamping out of these pieces cylinders having a diameter of 2.54 cm. These cylinders or "pucks" are washed successively in water (with intermediate squeezing steps) and 2-propanol to remove residual salt and emulsifier. These samples are then dried (either at ambient or elevated temperatures up to 65° C.). In some cases, the samples collapse upon drying and must be freeze-dried to recover a fully-expanded sample for testing.

A. Dynamic Mechanical Analysis (DMA)

DMA is used to determined the Tgs of polymers including polymeric foams. The sample pucks are analyzed using a Rhemometrics RSA-II dynamic mechanical analyzer set in compression mode using parallel plates 25 mm in diameter. Instrument parameters used are as follows:

Temperature step from ca. 120° C. to −50° C. in steps of 1.0° to 2.5° C., depending on the precision needed to define the transition point Soak intervals between temperature changes of 120–160 seconds Dynamic strain set at 0.7%

Frequently set at 1.0 radians/second

Autotension set in static force tracking dynamic force mode with initial static force set at 5 g.

The glass transition temperature is taken as the maximum point of the loss tangent (tan[δ]) versus temperature curve.

B. Yield Stress

Yield stress can be quantified by compressing a foam sample at a specific rate and at a specific temperature and measuring the resistance exerted by that sample to the compression. Typically, the data are formatted as a plot of stress on the y-axis and strain on the x-axis. Such plots typically show an initial linear response followed by a rapid loss in resistance to further compression at a point termed the "yield point". The yield point is defined as the intersection of the lines formed by the linear regions before and after the yield point. The yield stress is the stress value at that intersection. The analysis is performed using the same equipment defined in the preceding section (Rheometrics RSA-II) operating in a constant strain mode. In this mode, the temperature is set to 31° C. and the strain rate is set at 0.1% second. The sample is held at this temperature for at least 5 minutes prior to the initiation of compression to bring it to the defined temperature. The experiment is run for 10 minutes in compression followed by 10 minutes at the same rate of strain in the reverse direction. The data analysis is conducted as described above.

C. Density

Density is the weight of a given sample divided by its volume and may be determined by an appropriate standard method. Density measurements used herein involved weighing the cylindrical samples (pucks) used in the above measurements which had a diameter of 2.54 cm. The thickness of the sample was determined by measurement. The density was then calculated using the equation density=weight (mg)/(0.057×thickness (mm) expressed in units of mg/cc. The samples were typically washed in water and 2-propanol to remove salt and residual emulsifier from the sample prior to these measurements. The measured densities conformed closely to what is expected from the water-to-oil ratio of the HIPE from which the particular foam was derived, e.g., density=(1/(W:O ratio+1)) in units of g/cc.

V. Specific Examples

The following examples illustrate the preparation of HIPE foams useful in the present invention.

EXAMPLES 1–5

Preparation of Foams from HIPEs

Examples 1–5 are illustrative of low density having desirably low Tgs and desirably high yield stresses achieved by using a silicon-containing Tg lowering comonomer.

A) HIPE Preparation

The water phase is prepared consisting of 10% calcium chloride (anhydrous) and 0.05% potassium persulfate (initiator).

The oil phase is prepared according to the monomer ratios described in Table 1, all of which include an emulsifier for forming the HIPE. The preferred emulsifier used in these examples is diglycerol monooleate (DGMO) used at a level of 5–10% by weight of oil phase. The DGMO emulsifier (Grindsted Products; Brabrand, Denmark) comprises approximately 81% diglycerol monooleate, 1% other diglycerol monoesters, 3% polyglycerols, and 15% other polyglycerol esters, imparts a minimum oil phase/water phase interfacial tension value of approximately 2.5 dyne/cm and has a critical aggregation concentration of approximately 2.9 wt %.

To form the HIPE, the oil phase is placed in a 3" diameter plastic cup. The water phase is placed in a jacketed addition funnel held at about 50° C. The contents of the plastic cup are stirred using a Cafrano RZR50 stirrer equipment with a six-bladed stirrer rotating at about 300 rpm (adjustable by operator as needed). At an addition rate sufficient to add the water phase in a period of about 2 to 5 minutes, the water phase is added to the plastic cup with constant stirring. The cup is moved up and down as needed to stir the HIPE as it forms so as to incorporate all the water phase into the emulsion.

B) Polymerization/Curing of HIPE

The HIPE in the 3" plastic caps are capped and placed in an oven set at 65° C. overnight to cure and provide a polymeric HIPE foam.

C) Foam Washing and Dewatering

The cured HIPE foam is removed from the cup as a cylinder 3" in diameter and about 4" in length. The foam at this point has residual water phase (containing dissolved emulsifiers, electrolyte, initiator residues, and initiator) about 50–60 times (50–60×) the weight of polymerized monomers. The foam is sliced on a meat slicer to give circular pieces about 3 to about 8 mm in thickness. These pieces are washed in distilled water and compressed to remove the water 3 to 4 times. They are further washed in 2-propanol and compressed about 3 to 4 times. The pieces are then dried in an oven at 65° C. for 1 to 2 hours. In some cases, the foams collapse upon drying and must be freeze-dried from the water swollen state to recover fully expanded foams. Various shapes and sizes of foams may be prepared similarly by use of appropriately shaped vessels in which the HIPE is cured and/or appropriate cutting or shaping. The process for preparing the foams of the present invention may also be a continuous one, such as that described in U.S. Pat. No. 5,149,720, issued Sep. 22, 1992 to DesMarais et al. or copending U.S. patent application Ser. No. 08/370,694, filed by DesMarais on Jan. 10, 1995, the disclosure of each of which is incorporated by reference.

Specific nonlimiting examples of combinations of comonomers to make foams of the present invention are shown in Tables 1 and 2.

TABLE 1

Foam Composition and Properties.

| Example # | EHA % | DVB % | Silicon-containing monomer (%) | Yield Stress (psi) | Density (mg/cc) | Tg (° C.) |
|---|---|---|---|---|---|---|
| 1 | 55% | 40% | AETMS, 5% | 0.59 | 16 | 25° |
| 2 | 50% | 40% | AETMS, 10% | 0.72 | 20 | 22° |
| 3 | 50% | 40% | APTMS, 10% | 0.90 | 18 | 18° |
| 4 | 40% | 40% | APTMS, 20% | 0.79 | 15 | 24° |
| 5 | 30% | 40% | APTMS, 30% | 0.68 | 15 | 23° |

EHA = 2-ethylhexyl acrylate; available from Aldrich Chemical Corp of Milwaukee, WI.
DVB = divinyl benzene, based on 39–42% purity with 58–61% ethyl styrene impurity; available from Dow Chemical Corp. of Midland, MI.
AETMS = 2-(acryloxyethoxy)trimethylsilane.
APTMS = (3-acryloxypropyl)methylbis-(trimethylsiloxy)silane.

All silicon and germanium compounds used herein were obtained from Gelset, Inc. of Tullytown, Pa. unless otherwise noted.

EXAMPLES 6–14

Examples 6–14 are illustrative of low density foams having desirably low Tgs and high yield stresses achieved by using a polyfunctional silicon-containing crosslinking agent. The foams are prepared using the process described for making foams of Examples 1–5, and the oil phase components described in Table 2.

TABLE 2

Foam Composition and Properties.

| Example # | EHA % | DVB % | ISO % | Silicon-containing monomer (%) | Yield Stress (psi) | Density (mg/cc) | Tg (° C.) |
|---|---|---|---|---|---|---|---|
| 6 | 55% | 33% | 0% | BMAPTD, 12% | 0.44 | 18 | 19° |
| 7 | 55% | 33% | 0% | TUPMTS, 12% | 0.58 | 16 | 14° |
| 8 | 55% | 33% | 0% | TAS, 12% | 0.77 | 17 | 16° |
| 9 | 55% | 33% | 0% | TKMES, 12% | 0.90 | 17 | 26° |
| 10 | 50% | 33% | 0% | TKMES, 17% | 1.43 | 16 | 54° |
| 11 | 55% | 38% | 0% | TKMES, 7% | 0.71 | 16 | 33° |
| 12 | 55% | 28% | 0% | TKMES, 17% | 0.96 | 17 | 23° |
| 13 | 0% | 33% | 55% | TKMES, 12% | 1.68 | 13 | NM |

ISO = isoprene; available from Aldrich Chemical Corp. Because isoprene boils at 33° C., the HIPE preparation for Example 13 is carried out at 0–5° C. and the container is cured in a pressure vessel pressurized to 30 psi with argon. The pressure vessel is placed in the curing oven set at 65° C. for two days to effect curing.
BMAPTD = 1,3-bis(3-methylacryloxypropyl)tetramethyldisiloxane.
TUPMTS = 1,3,5-trivinyl-1,1,3,5,5-pentamethyltrisiloxane.
TAS = tetraallyl silane.
TKMES = tetrakis(methacryloxyethoxy)silane.
NM = Not Measured All silicon and germanium compounds used herein are obtained from Gelset, Inc. of Tullytown, Pa. unless otherwise noted.

In other examples, other alkyl acrylates are used in partial or total substitution for EHA, other crosslinkers are used in partial or total substitution for DVB, related analogs are used wherein germanium is used in partial or total substitution for silicon, and other emulsifiers including ditallowdimethylamonium methylsulfate are used in partial or total substitution for DGMO, as described hereinabove.

What is claimed is:

1. A polymeric foam material comprising at least 5% based on the weight of the foam, of one or more comonomer(s) selected from the group consisting of silicon-containing comonomers, germanium-containing comonomers, and mixtures thereof; characterized in that the polymeric foam materials has:

A) a density of less than 0.10 g/cc;
B) a glass transition temperature (Tg) of from −40° to 90° C.; and
C) a yield stress value at least 0.25 psi.

2. The polymeric foam material of claim 1 wherein the foam comprises from about 8% to about 50%, based on the total weight of the foam, of one or more comonomers(s) selected from the group consisting of silicon-containing comonomers, germanium-containing comonomers, and mixtures thereof.

3. The polymeric foam of claim 1 wherein the foam is hydrophilic and is capable of acquiring and distributing aqueous fluids.

4. The polymeric foam material of claim 3 wherein the foam has a specific surface area of at least about 0.01 m²/cc.

5. The polymeric foam material of claim 4 wherein the foam has a specific surface area of at least about 0.025 m²/cc.

6. The polymeric foam material of claim 3 wherein the foam has a Tg of from about 15° to about 50° C.

7. The polymeric foam material of claim 3 wherein the foam has a yield stress value of at least about 0.25 psi.

8. The polymeric foam material of claim 7 wherein the foam has a yield stress value of at least about 0.50 psi.

9. The polymeric foam material of claim 3 wherein the foam has an average cell size of not more than about 150 μm.

10. The polymeric foam material of claim 1 wherein the foam is hydrophobic.

11. The polymeric foam material of claim 10 wherein the foam has an average cell size of from about 10 μm to about 100 μm.

12. The polymeric foam material of claim 11 wherein the foam has an average cell size of from about 15 μm to about 35 μm.

13. The polymeric foam material of claim 10 wherein the foam has a Tg of from about 15° to about 50° C.

14. A polymeric foam material obtained from polymerizing a high internal phase water-in-oil emulsion, wherein the foam comprises at least about 5%, based on the weight of the foam, of one or more comonomer(s) selected from the group consisting of silicon-containing comonomers, germanium-containing comonomers, and mixtures thereof.

15. The polymeric foam material of claim 14 wherein the foam comprises from about 8% to about 50%, based on the total weight of the foam, of one or more comonomer(s) selected from the group consisting of silicon-containing comonomers, germanium-containing comonomers, and mixtures thereof.

16. The polymeric foam of claim 14 wherein the foam is hydrophilic and is capable of acquiring and distributing aqueous fluids.

17. The polymeric foam of claim 14 wherein the foam is hydrophobic.

18. The polymeric foam of claim 1 wherein the foam is prepared by the process comprising the steps of:

(A) forming a water-in-oil emulsion under low shear mixing from:
(1) an oil phase comprising:
(a) from about 80% to about 98% by weight of a monomer component capable of forming a copolymer having a Tg value of from about −40° C. to about 90° C., said monomer component comprising:
(i) at least about 5% by weight of a material selected from the group consisting of one or more comonomers containing silicon, one or more comonomers containing germanium, and mixtures thereof;
(ii) from about 0% to about 70% by weight of a substantially water-insoluble, monofunctional monomer capable of forming a homopolymer having a Tg of about 40° C. or less;
(iii) from about 0% to about 70% by weight of a substantially water-insoluble, monofunctional comonomer capable of imparting toughness about equivalent to that provided by styrene;
(iv) from about 0% to about 50% of a first substantially water-insoluble, polyfunctional crosslinking agent selected from the group consisting of divinyl benzene and analogs thereof; and
(v) from about 0% to about 15% of a second substantially water-insoluble, polyfunctional crosslinking agent selected from the group consisting of diacrylates and dimethacrylates of diols and analogs thereof; and
(b) from about 2% to about 20% by weight of an emulsifier component which is soluble in the oil phase and which is suitable for forming a stable water-in-oil emulsion;
(2) a water phase comprising from about 0.1% to about 20% by weight of a water-soluble electrolyte; and
(3) a volume to weight ratio of water phase to oil phase of at least about 10:1; and (B) polymerizing the monomer component in the oil phase of the water-in-oil emulsion to form the polymeric foam material.

19. The polymeric foam of claim 18, wherein the monomer component of the oil phase of the emulsion comprises from about 8 to about 50% of a material selected from the group consisting of one or more monofunctional comonomers comprising silicon, one or more monofunctional comonomers comprising germanium, and mixtures thereof.

20. The polymeric foam of claim 19, wherein the monomer component of the oil phase of the emulsion comprises a comonomer selected from the group consisting of (3-acryloxypropyl)methylbis-(trimethylsiloxy)silane, allyltriisopropyl silane, allyltriphenyl silane, bis(trimethylsilyl) itaconate, p-(t-butyldimethylsiloxy)styrene, methacrylamido-propyltriethoxysilane, methacryloxyethoxytrimethylsilane, (methacryloxymethyl)-dimethylethoxysilane, methacryloxytrimethyl silane, (2,4-pentadienyl)trimethylsilane, styrylethyltrimethoxysilane, 3-(N-styrylmethyl-2-aminoethylamino)propyltrimethoxysilane hydrochloride, (m,p-vinylbenzyloxy)trimethylsilane, vinyltrimethyl silane, vinyldimethylethyl silane, vinylpentamethyldisiloxane, vinyl trifluoromethyldimethyl silane, vinyltris(trimethylsiloxy)silane, vinyltriethyl germane, and mixtures thereof.

21. The polymeric foam of claim 18 wherein the monomer component of the oil phase of the emulsion comprises from about 20 to about 60% by weight of a non-silicon, non-germanium containing monofunctional monomer capable of forming a homopolymer having a Tg of about 40° C. or less.

22. The polymeric foam of claim 18 wherein the monomer component of the oil phase of the emulsion comprises from about 5 to about 80% by weight of a polyfunctional crosslinker that comprises silicon or germanium.

23. The polymeric foam of claim 22 wherein the polyfunctional crosslinker is selected from the group consisting of tetraallyl silane, tetrakis(2-methacryloxyethoxy)silane, 1,3-bis(3-methacryloxypropyl)tetramethyl-disiloxane, 1,3,5-trivinyl-1,1,3,5,5-pentamethyltri-siloxane, dimethoxydiallyl silane, bis(2-allyloxymethyl)-1-trimethylsiloxybutane, bis(methacryloxy)diphenylsilane, bis(methacryloxy) dimethyl silane, bis(4-styryl)dimethy-lsilane, diallyldiphenylsilane, diallyldimethylsilane, 1,3-diallyltetramethyldisiloxane, divinyltetramethyldisiloxane, hexavinyldisiloxane, bis(2-allyloxymethyl)phenethyl)-tetramethyldisiloxane, 1,5-divinylhexamethyltrisiloxane, tetraallyl germane, and mixtures thereof.

24. The polymeric foam of claim 22 wherein the monomer component of the oil phase of the emulsion comprises from about 10% to about 35% by weight of a polyfunctional crosslinking agent selected from the group consisting of divinyl benzene and analogs thereof.

* * * * *

UNITED STATES PATENT AND TRADEMARK OFFICE
CERTIFICATE OF CORRECTION

PATENT NO.    : 6,136,874
DATED         : October 24, 2000
INVENTOR(S)   : Dyer et al.

It is certified that error appears in the above-identified patent and that said Letters Patent is hereby corrected as shown below:

Title page,
Item [57], ABSTRACT,
Line 2, please delete "germination" and insert therefor -- germanium --.

Column 1,
Line 29, please delete "imbide" and insert therefor -- imbibe --.

Column 2,
Line 67, please delete "comprehensive" and insert therefor -- compressive --.

Column 3,
Line 31, please delete "corresponding" and insert therefor -- correspondingly --.

Column 7,
Line 43, please delete "Alteratively" and insert therefor -- Alternatively --.

Column 9,
Line 14, between "methacrylate" and "decyl" please insert therefor -- , -- (a comma).
Line 59, between "groups" and "are" please insert therefore -- and --.

Column 10,
Line 55, please delete "trimethyl" and insert therefor -- triethylene --.

Column 12,
Line 48, please delete "emulsifier" and insert therefor -- emulsion --.

Column 13,
Line 11, please delete "phase" and insert therefor -- phases --.
Line 15, please delete "of" and insert therefor -- or --.

Column 14,
Line 48, please delete "determined" and insert therefor -- determine --.
Line 50, please delete "Rhemometrics" and insert therefor -- Rheometrics --.
Line 60, please delete "Frequently" and insert therefor -- Frequency --.

UNITED STATES PATENT AND TRADEMARK OFFICE
CERTIFICATE OF CORRECTION

PATENT NO. : 6,136,874
DATED : October 24, 2000
INVENTOR(S) : Dyer et al.

It is certified that error appears in the above-identified patent and that said Letters Patent is hereby corrected as shown below:

Column 15,
Line 13, between "0.1%" and "second" please insert therefor -- / --.
Line 21, please delete "an" and insert therefore -- any --.
Line 42, between "density" and "having" please insert therefor -- foams --.
Line 64, please delete "equipment" and insert therefor -- equipped --.

Column 16,
Line 8, please delete "caps" and insert therefor -- cups --.
Line 23, between "oven" and "at" please insert therefor -- set --.
Line 57, please delete "Gelset" and insert therefor -- Gelest --.

Column 17,
Line 26, please delete "Gelset" and insert therefor -- Gelest --.
Lines 32-33, please delete "ditallowdimethylamonium" and insert therefor -- ditallowdimethylammonium --.
Line 36, after "5%" please insert therefor -- , -- (a comma).
Line 41, please delete "materials" and insert therefor -- material --.

Signed and Sealed this

Twenty-seventh Day of May, 2003

JAMES E. ROGAN
*Director of the United States Patent and Trademark Office*